United States Patent
Costa

(12) 
(10) Patent No.: US 7,887,826 B2
(45) Date of Patent: Feb. 15, 2011

(54) INSECT REPELLENT FABRIC

(75) Inventor: George Costa, Herts (GB)

(73) Assignee: Intelligent Fabic Technologies PLC, Hatfield (GB)

( * ) Notice: Subject to any disclaimer, the term of this patent is extended or adjusted under 35 U.S.C. 154(b) by 60 days.

(21) Appl. No.: 12/162,296

(22) PCT Filed: Jan. 29, 2007

(86) PCT No.: PCT/GB2007/000287

§ 371 (c)(1),
(2), (4) Date: Nov. 26, 2008

(87) PCT Pub. No.: WO2007/085856

PCT Pub. Date: Aug. 2, 2007

(65) Prior Publication Data

US 2009/0081267 A1 Mar. 26, 2009

(30) Foreign Application Priority Data

Jan. 27, 2006 (GB) ................................. 0601712.3

(51) Int. Cl.
*A01N 25/34* (2006.01)
*A01N 65/40* (2006.01)
*A01N 37/18* (2006.01)
*A01P 17/00* (2006.01)

(52) U.S. Cl. ....................... 424/403; 424/774; 514/617; 514/729

(58) Field of Classification Search ........................ None

See application file for complete search history.

(56) References Cited

U.S. PATENT DOCUMENTS

| 2002/0039593 A1* | 4/2002 | Tucci et al. ................. 424/411 |
| 2006/0188582 A1* | 8/2006 | Naylor Da Rocha Gomes ....................... 424/490 |

FOREIGN PATENT DOCUMENTS

| CA | 2675247 A1 | 8/2008 |
| EP | 0 348 550 A2 | 1/1990 |
| FR | 2 811 864 | 1/2002 |
| FR | 2 858 637 | 2/2005 |
| GB | 2 385 789 A | 9/2003 |
| GB | 2 434 592 B | 6/2009 |
| JP | 3-2101 | 1/1991 |
| JP | 3-148203 | 6/1991 |
| JP | 4352703 A | 12/1992 |
| JP | 5-132402 | 5/1993 |
| JP | 2000-328463 | 11/2000 |
| KR | 20020091968 A | 12/2002 |
| WO | WO 95/17091 | 6/1995 |
| WO | WO 98/23149 | 6/1998 |
| WO | WO 2005/018795 A1 | 3/2005 |

OTHER PUBLICATIONS

Barnard et al. (Journal of Medical Entomology. Jul. 2004; 41 (4): 726-730).*
Coats. Annual Review of Entomology. 1994 (39): 489-515).*
Office Actions for UK Patent No. GB 2 434 592 B.

* cited by examiner

*Primary Examiner*—Shanon A Foley
(74) *Attorney, Agent, or Firm*—Patterson Thuente Christensen Pedersen, P.A.

(57) ABSTRACT

An insect repellent fabric. The fabric comprises a fabric base and an active insect repellent ingredient. The active ingredient is contained within microcapsules and the fabric base is impregnated with the microcapsules. The preferred active ingredient is a Citronella extract or DEET.

12 Claims, No Drawings

INSECT REPELLENT FABRIC

RELATED APPLICATIONS

The present application is a national stage entry of PCT Application No. PCT/GB2007/000287, filed Jan. 29, 2007, which claims priority to Great Britain application GB 0601712.3, filed Jan. 27, 2006, the disclosures of which are hereby incorporated by reference in their entireties.

FIELD OF THE INVENTION

The present invention relates to an insect-repellent fabric.

BACKGROUND OF THE INVENTION

In order to render a fabric insect-repellent, one method, particularly adopted by the military, is to soak combat clothing in an insecticide, such as permethrin. However, this tends to make the garments uncomfortable and causes an unpleasant odor. Also, it has a limited period of effectiveness. It is also known to impregnate the heel and toe portions of socks with a scented material and to impregnate socks and certain sports clothing with natural remedies, such as Aloe Vera extract.

Currently, mosquitoes are one of the greatest causes of death in humans. One in 17 people alive today will be killed by mosquito bites. Worldwide, over 700 million people are infected by mosquitoes each year, with over 3 million dying. In the United Kingdom, biting insects can generally spoil holidays and can be a serious concern for parents with sensitive or allergic children.

SUMMARY OF THE INVENTION

It is an object of the invention to provide a textile article which is effective in repelling biting insects and which has a long lasting effect. It is a further object to provide a delivery mechanism which eliminates the need for sticky and malodorous, directly applied chemicals, which tend to be neither safe nor particularly effective. It is a further object to provide a safe and hypoallergenic inset repellent for children.

DETAILED DESCRIPTION

According to an embodiment the invention, an insect-repellent fabric comprises a fabric base and an active insect repellent ingredient, in which the active ingredient is contained within micro-capsules, and the fabric base is impregnated with the micro-capsules.

The microcapsules can be in the size range of about 1 µm to about 7 µm, and more about 2 µm to about 4 µm, and can have a mean diameter of about 3 µm.

In one embodiment of the invention, the fabric base is knitted (weft or warp), woven or spun-bonded from a spun yarn made from non-continuous short filaments and/or yarn made from continuous filaments. The material can be selected from polyester, nylon, cotton, or any suitable material and combinations thereof.

The fabric base is subjected to binding and finishing. The binding process can selectively bind the micro-capsules to the fibres and can comprise heating to a temperature in a range of about 40° C. to about 160° C., particularly of about 80° C. to about 120° C., for a period of at least 20 seconds, however, the precise parameters can be determined by the particular process and machinery being used. The binding process can be an ion-exchange process, for example.

The active ingredient can be selected from an extract of Citronella and DEET. One example material is para-menthane-3,8-diol; conveniently, this is isolated from a natural source (lemon eucalyptus oil), and then added to a non-reactive base oil. During this synthesis process, the plant extracts Limonene and Linalool, which are known sensitizers, are removed. The invention also extends to the example composition per se and in its encapsulated form.

The impregnated fabric is then cut to size for use in clothing manufacture or for use as an impregnated cloth for topical application of the micro-capsules. Alternatively, the fabric can be formed into a finished article first and then impregnated.

The invention provides a unique chemical repelling agent which provides a comparative level of efficacy to military specification DEET products. It also provides a chemical repelling agent specifically designed to eliminate or reduce allergens and sensitizers to ensure hypoallergenicity and safety for children. The delivery system of a microencapsulated active agent bound to a fabric at a molecular level, ensures effectiveness, consistency and durability.

Fragrance can also be incorporated, either in the same microcapsules as the active ingredient or in separate microcapsules.

The detection of the fragrance in use can serve as an indicator that the active ingredient is still present and effective.

The invention may be carried into practice in various ways and some specific embodiments will now be described by way of example.

A fabric is first prepared by knitting from non-continuous short filament synthetic spun yarn. While microencapsulated chemicals can be bound to other fibers, this has been found to be the most efficacious. This fabric is then sent to a binding shop for dying and micro-encapsulation.

The binding process uses an ionic based process to selectively bind the micro-capsules to the fabric. The process heats the ends of the fiber filaments to a point where they 'open' (like a flower). An ion-exchange process then drives the encapsulated active component into the open fabric pore, which then closes around it, binding it in place.

The active ingredient or component is para-menthane-3,8-diol. It is a modified natural extract of Eucalyptus Maculata Citriodora. It is dissolved in isopropyl myristate and subjected to a micro-encapsulation process, using a Melamine based polymer in an aqueous solution at a mean micron size of about 3. The resultant product is then combined with a soft acrylic binder in anionic form and applied to the fabric base by means of a paddling mangle, and is then dried at about 140° C. The application can also be made via an exhaust process using a non-ionic soft acrylic binder or a spraying or foaming process using a soft acrylic binder in anionic form.

The invention claimed is:

1. An insect-repellent fabric comprising:
   a fabric base; and
   an active insect-repellent ingredient, wherein the active ingredient is para-menthane-3,8-diol isolated from a natural source and added to a non-reactive base oil, the non-reactive base oil being substantially free of limonene and linalool,
   wherein the para-menthane-3,8-diol is contained within microcapsules, and the fabric base is impregnated with the microcapsules.

2. The fabric according to claim 1, wherein the microcapsules are in a size range of from about 1 µm to about 7 µm.

3. The fabric according to claim 1, wherein the fabric base is made from a spun yarn made from non-continuous short filaments.

4. The fabric according to claim 1, wherein the fabric base is made from yarn made from continuous filaments.

5. The fabric according to claim 1, wherein the fabric base is made by a process selected from the group consisting of knitting, weaving, spin-bonding, and combinations thereof.

6. The fabric according to claim 1, wherein the fabric base is made from a material selected form the group consisting of polyester, nylon, cotton and combinations thereof.

7. A method of producing an insect repellent fabric, the method comprising:
    impregnating a fabric base with microcapsules, the microcapsules containing para-menthane-3,8-diol as an active insect repellent ingredient, wherein the para-menthane-3,8-diol is isolated from a natural source and added to a non-reactive base oil, the non-reactive base oil being substantially free of limonene and linalool.

8. The method according to claim 7, wherein the fabric base is subjected to binding process and finishing process.

9. The method according to claim 7, wherein the binding process binds the microcapsules to the fibers in the fabric base, the bonding process comprising heating to a temperature in a range of from about 40° C. to about 160° C., for a period of at least 20 seconds.

10. The method according to claim 8, wherein the binding process comprises an ion-exchange process.

11. An insect repellent material comprising an active insect repellent ingredient contained within microcapsules, wherein the active insect repellent ingredient comprises para-menthane-3,8-diol isolated from a natural source and added to a non-reactive base oil, the non-reactive base oil being substantially free of limonene and linalool.

12. The material according to claim 11, wherein the microcapsules are in a size range of from about 1 μm to about 7 μm.

\* \* \* \* \*